United States Patent
Patel et al.

(10) Patent No.: US 6,869,963 B2
(45) Date of Patent: Mar. 22, 2005

(54) STABLE PHARMACEUTICAL COMPOSITIONS CONTAINING AN ACE INHIBITOR

(75) Inventors: Ashish Anilbhai Patel, Kendall Park, NJ (US); Pablo Davila, East Windsor, NJ (US)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/618,548

(22) Filed: Jul. 11, 2003

(65) Prior Publication Data

US 2005/0009806 A1 Jan. 13, 2005

(51) Int. Cl.$^7$ ............................................... A61K 31/47
(52) U.S. Cl. ...................................................... 514/307
(58) Field of Search ........................... 514/212.07, 221, 514/307, 409, 412, 423, 563

(56) References Cited

U.S. PATENT DOCUMENTS

| | | | |
|---|---|---|---|
| 4,344,949 A | 8/1982 | Hoefle et al. ................ | 242/258 |
| 4,743,450 A | 5/1988 | Harris et al. ................. | 424/440 |
| 4,793,998 A | 12/1988 | Murthy et al. ............... | 424/440 |
| 4,830,853 A | 5/1989 | Murthy et al. ............... | 424/440 |
| 5,562,921 A | 10/1996 | Sherman ...................... | 424/465 |
| 5,684,016 A | 11/1997 | Henning et al. ............. | 514/307 |
| 5,738,872 A | 4/1998 | Ortyl et al. .................. | 424/452 |
| 5,747,504 A | 5/1998 | Henning et al. ............. | 514/307 |
| 5,855,912 A | 1/1999 | Ortyl et al. .................. | 424/452 |
| 6,113,942 A | 9/2000 | Ortyl et al. .................. | 424/452 |
| 6,300,361 B1 | 10/2001 | Vivilecchia et al. ......... | 514/409 |
| 6,300,362 B1 | 10/2001 | Vivilecchia et al. ......... | 514/409 |
| 6,509,350 B2 | 1/2003 | Vivilecchia et al. ......... | 514/307 |
| 2003/0027837 A1 | 2/2003 | Sherman ...................... | 514/307 |

OTHER PUBLICATIONS

Remington's Pharmaceutical Sciences, 16$^{th}$ ed., published 1980, pp 1560–1563.*
Handbook of Pharmaceutical Excipients, published 1986 by the Ameerican Pharmaceutical Assn., pp 134–137.*

* cited by examiner

*Primary Examiner*—Raymond J. Henley, III
(74) *Attorney, Agent, or Firm*—John D. Thallemer; Diane E. Furman

(57) ABSTRACT

A stable pharmaceutical composition comprising about 1 wt. % to about 80 wt. % of an ACE inhibitor or a pharmaceutical acceptable salt thereof, about 1 wt. % to about 70 wt. % of an alkali or alkaline earth metal carbonate, and about 1 wt. % to about 80 wt. % of hydroxypropyl cellulose, wherein the ACE inhibitor is selected from the group consisting of quinapril, enalapril, spirapril, ramipril, perindopril, indolapril, lisinopril, alacepril, trandolapril, benazapril, libenzapril, delapril, cilazapril and combinations thereof; wherein the formation of an internal cyclization product, and/or ester hydrolysis product, and/or oxidation product, has been reduced or eliminated, and the weight percents are based on the total weight of the pharmaceutical composition. The stabilized pharmaceutical compositions of the invention exhibit a number of advantages as follows: (i) the ACE inhibitor or a pharmaceutical acceptable salt thereof present in the compositions is preserved from degradation; (ii) the compositions exhibit extended shelf-life under normal storage conditions; (iii) the effect of moisture on the compositions is minimized; (iv) the compositions exhibit minimal, if any, discoloration over a significant period of time; and (v) the compositions exhibit minimal, if any, instability when employed in the presence of colorants.

17 Claims, No Drawings

US 6,869,963 B2

STABLE PHARMACEUTICAL COMPOSITIONS CONTAINING AN ACE INHIBITOR

FIELD OF THE INVENTION

The invention relates to a stable pharmaceutical composition containing an angiotensin converting enzyme (ACE) inhibitor, an alkali or alkaline earth metal carbonate, and hydroxypropyl cellulose, wherein the formation of an internal cyclization product and/or ester hydrolysis product and/or oxidation product, has been reduced or eliminated.

BACKGROUND OF THE INVENTION

There are a number of pharmaceutical compositions which suffer from instability problems due to the fact that the active component is susceptible to certain types of degradation, thereby diminishing their attractiveness and, in some cases, rendering them unsuitable from a commercial standpoint. For example, several ACE inhibitor-containing compositions suffer from this drawback since certain ACE inhibitors degrade readily in pharmaceutical dosage forms. For example, quinapril, enalapril, and spirapril degrade readily in dosage form to a diketo piperazine (the internal cyclization product) and a diacid (the ester hydrolysis product). It is believed that one or more of these types of degradation including oxidation causes the discoloration in pharmaceutical compositions containing ACE inhibitors. In addition, the degradation products may result in decreased drug effectiveness in such pharmaceutical compositions. Accordingly, in view of their usefulness in treating hypertension, a number of research endeavors have been directed to overcoming the instability problem associated with pharmaceutical compositions containing ACE inhibitors, with limited success.

Various methods of improving the stability of certain ACE inhibitors have been disclosed. U.S. Pat. No. 4,743,450 discloses that certain ACE inhibitors, and in particular, quinapril and its acid addition salts can be stabilized by making solid compositions that include an alkali or alkaline earth metal carbonate, preferably magnesium carbonate, and a saccharide, specifically a sugar, such as mannitol or lactose. U.S. Pat. No. 4,793,998 discloses that certain ACE inhibitors, and in particular, quinapril and its acid addition salts can be stabilized by making solid compositions that include ascorbic acid, and optionally one or more acids selected from citric, fumaric and maleic acids. U.S. Pat. No. 4,830,853 discloses that certain ACE inhibitors, and in particular, quinapril and its acid addition salts can be stabilized by making solid compositions that include ascorbic acid or a metal or ammonium ascorbate.

Although each of the above patents represents an attempt to overcome the instability problems associated with pharmaceutical compositions containing an ACE inhibitor, there still exists a need for improving the stability of such pharmaceutical compositions, especially in the presence of moisture.

SUMMARY OF THE INVENTION

The invention provides a stable pharmaceutical composition comprising about 1 wt. % to about 80 wt. % of an ACE inhibitor or a pharmaceutical acceptable salt thereof, about 1 wt. % to about 70 wt. % of an alkali or alkaline earth metal carbonate, and about 1 wt. % to about 80 wt. % of hydroxypropyl cellulose, wherein the ACE inhibitor is selected from the group consisting of quinapril, enalapril, spirapril, ramipril, perindopril, indolapril, lisinopril, alacepril, trandolapril, benazapril, libenzapril, delapril, cilazapril and combinations thereof; wherein the formation of an internal cyclization product, and/or ester hydrolysis product, and/or oxidation product, has been reduced or eliminated and the weight percents are based on the total weight of the pharmaceutical composition.

According to another aspect, the invention provides a method of preparing a stable pharmaceutical composition comprising about 1 wt. % to about 80 wt. % of an ACE inhibitor or a pharmaceutical acceptable salt thereof, about 1 wt. % to about 70 wt. % of an alkali or alkaline earth metal carbonate, and about 1 wt. % to about 80 wt. % of hydroxypropyl cellulose, wherein the ACE inhibitor is selected from the group consisting of quinapril, enalapril, spirapril, ramipril, perindopril, indolapril, lisinopril, alacepril, trandolapril, benazapril, libenzapril, delapril, cilazapril, and combinations thereof; wherein the formation of an internal cyclization product, and/or ester hydrolysis product, and/or oxidation product, has been reduced or eliminated, and the weight percents are based on the total weight of the pharmaceutical composition, said method comprising:

(a) mixing the ACE inhibitor or a pharmaceutical acceptable salt thereof, an alkali or alkaline earth metal carbonate, hydroxypropyl cellulose, and optionally one or more excipients, to form a premix;

(b) adding a solvent, and optionally one or more excipients, to the premix formed in Step (a) to form a wet granulation;

(c) drying the wet granulation to form granules, and optionally milling the granules; and (d) optionally mixing one or more excipients with the granules to form a pharmaceutical composition.

The stabilized pharmaceutical compositions of the invention exhibit a number of advantages as follows: (i) the ACE inhibitor or a pharmaceutical acceptable salt thereof present in the compositions is preserved from degradation; (ii) the compositions exhibit extended shelf-life under normal storage conditions; (iii) the effect of moisture on the compositions is minimized; (iv) the compositions exhibit minimal, if any, discoloration over a significant period of time; and (v) the compositions exhibit minimal, if any, instability when employed in the presence of colorants.

DESCRIPTION OF THE INVENTION

The pharmaceutical composition of the invention contains an ACE inhibitor or a pharmaceutical acceptable salt thereof, an alkali or alkaline earth metal carbonate, and hydroxypropyl cellulose. The ACE inhibitor is selected from quinapril, enalapril, spirapril, ramipril, perindopril, indolapril, lisinopril, alacepril, trandolapril, benazapril, libenzapril, delapril, and cilazapril. A combination of ACE inhibitors may also be used. Preferably, the ACE inhibitor is selected from quinapril, enalapril, and spirapril. More preferably, the ACE inhibitor is quinapril hydrochloride. It is noted that the ACE inhibitor may form a salt with various inorganic and organic acids and bases, which salts may be prepared by conventional methods.

The amount of ACE inhibitor or a pharmaceutical acceptable salt thereof in the pharmaceutical compositions is preferably from about 1 wt. % to about 80 wt. %, based on the total weight of the pharmaceutical composition. More preferably, the amount of ACE inhibitor or a pharmaceutical acceptable salt thereof is from about 5 wt. % to about 50 wt. %, most preferably about 10 wt. % to about 15 wt. %. As indicated above, ACE inhibitors including pharmaceutical acceptable salts thereof are known and their usefulness in treating hypertension is also well known. Accordingly, the daily dosages at which said ACE inhibitors or pharmaceutical acceptable salts thereof are employed as well as typical unit dosages of said ACE inhibitors or pharmaceutical acceptable salts thereof are well documented in the literature. Preferably, the ACE inhibitor or a pharmaceutical acceptable salt thereof is present in the pharmaceutical composition in an amount of from about 1 mg to about 100 mg.

The alkali or alkaline earth metal carbonate is a salt which is prepared by reacting an alkali metal or alkaline earth metal with carbonic acid. The alkali metal is selected from lithium, sodium, potassium, rubidium, cesium and francium. The alkaline earth metal is selected from magnesium, calcium, barium, strontium and radium. Magnesium, calcium and sodium are the preferred metals. Most preferably, the metal is magnesium.

The amount of the alkali or alkaline earth metal carbonate in the pharmaceutical compositions is from about 1 wt. % to about 70 wt. %, based on the total weight of the pharmaceutical composition. Preferably, the amount of the alkali or alkaline earth metal carbonate is from about 10 wt. % to about 60 wt. %, more preferably about 45 wt. % to about 55 wt. %.

Hydroxypropyl cellulose is a partially substituted poly (hydroxypropyl) ether of cellulose. Hydroxypropyl cellulose is commercially available in a number of different grades which have different solution viscosities. The molecular weight of the hydroxypropyl cellulose ranges from about 50,000 to about 1,250,000. A preferred hydroxypropyl cellulose is available from Aqualon under the trademark KLUCEL. Suitable grades of hydroxypropyl cellulose include the following:

1) KLUCEL EF having a molecular weight of about 80,000;
2) KLUCEL LF having a molecular weight of about 95,000;
3) KLUCEL JF having a molecular weight of about 140,000;
4) KLUCEL GF having a molecular weight of about 370,000;
5) KLUCEL MF having a molecular weight of about 850,000; and
6) KLUCEL HF having a molecular weight of about 1,150,000.

Preferably, the hydroxypropyl cellulose is a low-substituted hydroxypropyl cellulose. The low-substituted hydroxypropyl cellulose (L-HPC) useful in the pharmaceutical compositions of the invention is available in a number of different grades which have different particle sizes and substitution levels, and which are classified on the basis of their % hydroxypropoxy content. When dried at 105° C. for 1 hour, the L-HPC contains from about 5% to about 16% of hydroxypropoxy groups, preferably from about 10% to about 13% of hydroxypropoxy groups. Suitable grades of L-HPC include the following:

1) LH-11 having a hydroxypropoxy content of 11% and an average particle size of 50 microns;
2) LH-21 having a hydroxypropoxy content of 11% and an average particle size of 40 microns;
3) LH-31 having a hydroxypropoxy content of 11% and an average particle size of 25 microns;
4). LH-22 having a hydroxypropoxy content of 8% and an average particle size of 40 microns;
5) LH-32 having a hydroxypropoxy content of 8% and an average particle size of 25 microns;
6) LH-20 having a hydroxypropoxy content of 13%, and an average particle size of 40 microns; and
7) LH-30 having a hydroxypropoxy content of 13%, and an average particle size of 25 microns.

Preferred L-HPCs are commercially-available from Shin-Etsu Chemical Company under the trade designation L-HPC Grade LH-21 and LH-11.

The amount of hydroxypropyl cellulose in the pharmaceutical compositions is from about 1 wt. % to about 80 wt. %, based on the total weight of the pharmaceutical composition. Preferably, the amount of hydroxypropyl cellulose is from about 10 wt. % to about 50 wt. %, more preferably about 30 wt. % to about 40 wt. %.

The stabilized pharmaceutical compositions of the invention may also contain one or more excipients that are normally employed in pharmaceutical formulations, the only qualification being that they must not deleteriously affect the stability of the pharmaceutical compositions. Examples of such excipients are surfactants, diluents, binders, amino acids, solubilizers, disintegrants, fillers, lubricants, buffers, stabilizers, colorants, dyes, anti-oxidants, anti-adherents, preservatives and glidants. A combination of excipients may also be used. Such excipients are known to those skilled in the art, and thus, only a limited number will be specifically referenced.

Examples of fillers include microcrystalline cellulose, dibasic calcium phosphate dihydrate, calcium sulfate trihydrate and calcium sulfate dehydrate. A combination of fillers may also be used. Preferably, the pharmaceutical composition of the invention does not contain a saccharide, specifically a sugar, such as lactose or mannitol. In addition, preferably the pharmaceutical composition of the invention does not contain starch.

Examples of lubricants include magnesium stearate, sodium stearate, calcium stearate, zinc stearate, talc, propylene glycol, PEG, stearic acid, vegetable oil, sodium benzoate, sodium lauryl sulfate, magnesium lauryl sulfate, mineral oil and polyoxyethylene monostearate. A combination of lubricants may also be used. A preferred lubricant is magnesium stearate.

Examples of binders include gums, such as gum tragacanth, acacia gum and gelatin; microcrystalline cellulose, e.g., products known under the registered trademarks Avicel, Filtrak, Heweten or Pharmacel, hydroxyethyl cellulose and hydroxypropylmethyl cellulose; and polyvinyl pyrrolidone, e.g., Povidone.

Examples of glidants include silica, magnesium trisilicate, powdered cellulose, talc, calcium silicate, and tribasic calcium phosphate. Colloidal silica, e.g., Aerosil, is particularly preferred.

Examples of disintegrants include:
(i) cross-linked polyvinylpyrrolidones, e.g., crospovidones, such as Polyplasdone® XL and Kollidon® CL;
(ii) alginic acid and sodium alginate;
(iii) methacrylic acid-divinylbenzene co-polymer salts, e.g., Amberlite® IRP-88; and
(iv) cross-linked sodium carboxymethylcellulose, available as, e.g., Ac-di-sol®, Primellose®, Pharmacel® XL, Explocel® and Nymcel® ZSX.

Additional disintegrants also include hydroxypropylmethyl cellulose, croscarmellose sodium, polacrillin potassium, polyacrylates, such as Carbopol®, magnesium aluminium silicate and bentonite.

The pharmaceutical compositions of the invention can be prepared by any of the conventionally employed processing techniques such as dry granulation or wet granulation process. Wet granulation is preferably chosen to ensure a homogeneous distribution of the ACE, alkali or alkaline earth metal carbonate, and low-substituted hydroxypropyl cellulose.

In one embodiment of the invention, the pharmaceutical composition is prepared by a process comprising:
(a) mixing the ACE inhibitor or a pharmaceutical acceptable salt thereof, an alkali or alkaline earth metal carbonate, hydroxypropyl cellulose, and optionally one or more excipients, to form a premix;
(b) adding a solvent, and optionally one or more excipients, to the premix formed in Step (a) to form a wet granulation;
(c) drying the wet granulation to form granules, and optionally milling the granules; and
(d) optionally mixing one or more excipients with the granules to form a eutical composition.

Examples of solvents to be used in the wet granulation process include water, methanol, isopropanol, acetone and ethylene chloride. A combination of solvents may also be used. Preferably, the solvent is water.

Drying techniques useful for drying the granulation include spray-drying, fluid bed, flash drying, ring drying, micron drying, tray drying, vacuum drying, radio-frequency drying and microwave drying.

The pharmaceutical compositions of the invention may be in the form of a capsule, caplet, powder, disc or tablet. In a preferred embodiment, the pharmaceutical compositions are in the form of a tablet.

The following non-limiting examples illustrate further aspects of the invention.

EXAMPLE 1

Preparation of Quinapril Hydrochloride 40 mg Tablets.

| Item # | Ingredients | mg/tablet |
|---|---|---|
| 1 | Quinapril Hydrochloride | 43.33 |
| 2 | Magnesium Carbonate | 200.0 |
| 3 | Microcrystalline Cellulose pH 102 | 0.0 |
| 4 | L-HPC | 136.67 |
| 5 | Crospovidone | 16.0 |
| 6 | Magnesium Stearate | 4.0 |
| 7 | Methocel E15 LV | 8.0 |
| 8 | Triethyl Citrate | 0.8 |
| 9 | Opadry Beige YS-1-2718 | 8.0 |
| 10 | Purified Water | q.s. |
| Total | | 416.8 |

The tablet composition was prepared by:
(a) mixing quinapril hydrochloride, magnesium carbonate, and L-HPC to form a premix;
(b) adding water to the premix formed in Step (a) to form a wet granulation under high shear granulation conditions;
(c) drying the wet granulation in a fluid bed, and co-milling the dried granules;
(d) V-blending the crospovidone and magnesium stearate with the granules to form a composition which is compressed on a Manesty Beta Press to form tablets; and
(e) coating the tablets formed in Step (d) with Methocel and triethyl citrate using a Accela Cota; and
(f) color coating the tablets formed in Step (e) with Opadry Beige using an Accela Cota.

EXAMPLE 2

Preparation of Quinapril Hydrochloride 40 mg Tablets.

| Item # | Ingredients | mg/tablet |
|---|---|---|
| 1 | Quinapril Hydrochloride | 43.33 |
| 2 | Magnesium Carbonate | 200.0 |
| 3 | Microcrystalline Cellulose pH 102 | 136.67 |
| 4 | L-HPC | 0.0 |
| 5 | Crospovidone | 16.0 |
| 6 | Magnesium Stearate | 4.0 |
| 7 | Methocel E15 LV | 8.0 |
| 8 | Triethyl Citrate | 0.8 |
| 9 | Opadry Beige YS-1-2718 | 8.0 |
| 10 | Purified Water | q.s. |
| Total | | 416.8 |

The quinapril tablets were prepared according to the procedure set forth in Example 1.

EXAMPLE 3

Preparation of Quinapril Hydrochloride 40 mg Tablets.

| Item # | Ingredients | mg/tablet |
|---|---|---|
| 1 | Quinapril Hydrochloride | 43.33 |
| 2 | Magnesium Carbonate | 200.0 |
| 3 | Microcrystalline Cellulose pH 102 | 68.34 |
| 4 | L-HPC | 68.33 |
| 5 | Crospovidone | 16.0 |
| 6 | Magnesium Stearate | 4.0 |
| 7 | Methocel E15 LV | 8.0 |
| 8 | Triethyl Citrate | 0.8 |
| 9 | Opadry Beige YS-1-2718 | 8.0 |
| 10 | Purified Water | q.s. |
| Total | | 416.8 |

The quinapril tablets were prepared according to the procedure set forth in Example 1.

EXAMPLE 4

Preparation of Quinapril Hydrochloride 40 mg Tablets.

| Item # | Ingredients | mg/tablet |
|---|---|---|
| 1 | Quinapril Hydrochloride | 43.33 |
| 2 | Magnesium Carbonate | 200.0 |
| 3 | Microcrystalline Cellulose pH 102 | 100.0 |
| 4 | L-HPC | 36.67 |
| 5 | Crospovidone | 16.0 |
| 6 | Magnesium Stearate | 4.0 |
| 7 | Methocel E15 LV | 8.0 |
| 8 | Triethyl Citrate | 0.8 |
| 9 | Opadry Beige YS-1-2718 | 8.0 |
| 10 | Purified Water | q.s. |
| Total | | 416.8 |

The quinapril tablets were prepared according to the procedure set forth in Example 1.

EXAMPLE 5

The stability of the tablets prepared in Examples 1–4 was determined by the amount of degradation products according at 40° C. and 75% relative humidity.

TABLE 1

| Tablet | Quinapril (%) | Degradation Product Quinaprilate (wt. %) | Degradation Product DKP (wt. %) |
|---|---|---|---|
| Example 1 | 99.9 | 0.733 | 0.173 |
| Example 2 | 91.5 | 2.281 | 0.132 |
| Example 3 | 92.7 | 1.421 | 0.138 |
| Example 4 | 96.8 | 0.924 | 0.140 |

The test results in Table 1 clearly show that Example 2 which was prepared with magnesium carbonate but without hydroxypropyl cellulose had a significantly high level of degradation product quinaprilate.

While the invention has been described with particular reference to certain embodiments thereof, it will be understood that changes and modifications may be made by those of ordinary skill within the scope and spirit of the following claims:

What is claimed is:

1. A stable pharmaceutical composition comprising about 1 wt. % to about 80 wt. % of quinapril or a pharmaceutical acceptable salt thereof, about 1 wt. % to about 70 wt. % of an alkali or alkaline earth metal carbonate, and about 1 wt. % to about 80 wt. % of a low-substituted hydroxypropyl cellulose, wherein the weight percents are based on the total weight of the pharmaceutical composition.

2. The composition according to claim 1, wherein the quinapril is quinapril hydrochloride.

3. The composition according to claim 1, wherein the amount of quinapril or a pharmaceutical acceptable salt thereof is from about 5 wt. % to about 50 wt. %, based on the total weight of the pharmaceutical composition.

4. The composition according to claim 3, wherein the amount of quinapril or a pharmaceutical acceptable salt thereof is from about 10 wt. % to about 15 wt. %, based on the total weight of the pharmaceutical composition.

5. The composition according to claim 1, wherein the alkali metal is selected from the group consisting of lithium, sodium, potassium, rubidium, cesium and francium.

6. The composition according to claim 1, wherein the alkaline earth metal is selected from the group consisting of magnesium, calcium, barium, strontium and radium.

7. The composition according to claim 6, wherein the alkaline earth metal is magnesium.

8. The composition according to claim 1, wherein the amount of the alkali or alkaline earth metal carbonate is from about 10 wt. % to about 60 wt. %, based on the total weight of the pharmaceutical composition.

9. The composition according to claim 8, wherein the amount of the alkali or alkaline earth metal carbonate is from about 45 wt. % to about 55 wt. %, based on the total weight of the pharmaceutical composition.

10. The composition according to claim 1, wherein the low-substituted hydroxypropyl cellulose when dried at 105° C. for 1 hour contains 5–16% of hydroxypropoxy groups.

11. The composition according to claim 10, wherein the low-substituted hydroxypropyl cellulose when dried at 105° C. for 1 hour contains 10–13% of hydroxypropoxy groups.

12. The composition according to claim 1, wherein the low-substituted hydroxypropyl cellulose is selected from the group consisting of: LH-11 having a hydroxypropoxy content of 11% and an average particle size of 50 microns; LH-21 having a hydroxypropoxy content of 11% and an average particle size of 40 microns; LH-31 having a hydroxypropoxy content of 11%, and an average particle size of 25 microns; LH-22 having a hydroxypropoxy content of 8%, and an average particle size of 40 microns; LH-32 having a hydroxypropoxy content of 8%, and an average particle size of 25 microns; LH-20 having a hydroxypropoxy content of 13%, and an average particle size of 40 microns; and LH-30 having a hydroxypropoxy content of 13%, and an average particle size of 25 microns.

13. The composition according to claim 12, wherein the L-HPC is LH-21 or LH-11.

14. The composition according to claim 1, wherein the low-substituted hydroxypropyl cellulose is present in an amount of from about 10 wt. % to about 50 wt. %.

15. The composition according to claim 14, wherein the low substituted hydroxypropyl cellulose is present in an amount of from about 30 wt. % to about 40 wt. %.

16. The composition according to claim 1, which is in the form selected from the group consisting of a tablet, granules, bar, block, disc, capsule, caplet and powder.

17. A method of preparing a stable pharmaceutical composition comprising about 1 wt. % to about 80 wt. % of quinapril or a pharmaceutical acceptable salt thereof, about 1 wt. % to about 70 wt. % of an alkali or alkaline earth metal carbonate, and about 1 wt. % to about 80 wt. % of a low-substituted hydroxypropyl cellulose, wherein the weight percents are based on the total weight of the pharmaceutical composition, said method comprising:

(a) mixing quinapril or a pharmaceutical acceptable salt thereof, an alkali or alkaline earth metal carbonate, a low substituted hydroxypropyl cellulose, and optionally one or more excipients, to form a premix;

(b) adding a solvent, and optionally one or more excipients, to the premix formed in Step (a) to form a wet granulation;

(c) drying the wet granulation to form granules, and optionally milling the granules; and (d) optionally mixing one or more excipients with the granules to form a pharmaceutical composition.

* * * * *